United States Patent [19]

Rademacher et al.

[11] Patent Number: 5,869,424
[45] Date of Patent: Feb. 9, 1999

[54] PLANT GROWTH RETARDANTS IN COMBINATION WITH INHIBITORS OF ETHYLENE BIOSYNTHESIS OR ACTION

[75] Inventors: Wihelm Rademacher, Limburgerhof, Germany; Charles W. Helpert, Durham; Charles W. Finch, Garner, both of N.C.; Mary Callan, Limburgerhof, Germany; Hans von Amsberg, Chapel Hill, N.C.; Johannes Jung, Limburgerhof; Peter Eberhard Schott, Neustadt, both of Germany

[73] Assignee: BASF Corporation, Mount Olive, N.J.

[21] Appl. No.: 770,788

[22] Filed: Dec. 20, 1996

Related U.S. Application Data

[60] Provisional application No. 60/009,298 Dec. 21, 1995.
[51] Int. Cl.$^6$ .......................... A01N 37/00; A01N 37/02; A01N 37/14; A01N 43/40
[52] U.S. Cl. ........................ 504/130; 504/147; 504/148; 504/248; 504/319; 71/DIG. 1
[58] Field of Search ................................. 504/130, 147, 504/248, 319, 320, 148; 71/DIG. 1

[56] References Cited

U.S. PATENT DOCUMENTS

| | | | |
|---|---|---|---|
| 3,787,198 | 1/1974 | Hagimoto et al. | 504/134 |
| 3,876,782 | 4/1975 | Kishino et al. | 514/113 |
| 3,894,123 | 7/1975 | Kishino et al. | 558/174 |
| 3,928,586 | 12/1975 | Sledzinski et al. | 514/136 |
| 3,970,728 | 7/1976 | Kishino et al. | 558/185 |
| 4,002,458 | 1/1977 | Hofacker | 71/27 |
| 4,124,227 | 11/1978 | Ruis | 503/224 |
| 4,181,715 | 1/1980 | Kondo et al. | 424/122 |
| 4,217,130 | 8/1980 | Tsurata et al. | 504/287 |
| 4,220,464 | 9/1980 | Martin | 504/312 |
| 4,227,918 | 10/1980 | Hofer et al. | 504/350 |
| 4,277,364 | 7/1981 | Shasha et al. | 56/10.8 |

(List continued on next page.)

FOREIGN PATENT DOCUMENTS

| | | |
|---|---|---|
| 0 535 415 A1 | 10/1992 | European Pat. Off. |
| 2 081 700 | 7/1991 | United Kingdom. |
| 9307746 | 4/1993 | WIPO. |

OTHER PUBLICATIONS

Written Opinion International Application No. PCT/US96/20596, Filed 20 Dec. 1996.

F. Bangerth "The Effect of a Substituted Amino Acid on Ethylene Biosynthesis, Respiration, Ripening and Preharvest Drop of Apple Fruits" *Chemical Abstract* vol. 89, No. 1 (Jan., 1979) Abstracts No: 454608 (*J.Am.Soc.Hortic.Sci.* vol. 103, No. 3 (1978) pp. 401–404.

D.W. Greene. "Effect of Silver Nitrate, Aminoethoxyvinylglcine, and Gibberellins A4+7 plus 6–Benzylamino Purine on Fruit Set and Development of 'Delicious' Apples" *Chemical Abstracts*, vol. 93, No. 21 (Nov., 1980) Abstract No. 199123 (*J.Am.Soc.Hortic.Sci*vol. 105, No. 5 (1980) pp. 717–720.

Database WPI, Section CH, Week 9546 *Derwent Publications Ltd.*, Class C03, AN 95–351558 AU 136259 95 A (Rhone Poulenc Agrcchimie} {Sep., 1995} US 5 478 796 A (Dec. 1995).

Abeles; "Abscission: Role of Cellulase";(1969) 44:447–452; *Plant Physiol.*

Amagasa, et al.; "The Mode of Flower–Inhibiting Action of Ethylene in Pharbitis nil"; (1987) 28(6):1159–1161; *Plant Cell Physiol.*

Atsmon, et al; "Comparative effects of gibberellin, silver nitrate and aminoethoxyvinly glycine on sexual tendency and ethylene evolution in the cucumber plant"; (1979) 20(8):1547–1555; *Plant and Cell Physiol.*

BASF Corporation; "Pix® plant regulator—Results in Cotton (Southwest)"; (1987); *Technical Information Bulletin No. 8626.*

(List continued on next page.)

*Primary Examiner*—John Pak
*Attorney, Agent, or Firm*—George A. Gilbert

[57] ABSTRACT

Provided are compositions and methods of improving a plant growth factor. The compositions and methods contain combinations of plant growth regulators such as plant growth retardants and inhibitors of ethylene biosynthesis or action. The ethylene inhibitors comprise substituted oxime-ethers having the general formula:

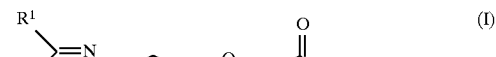

(I)

or

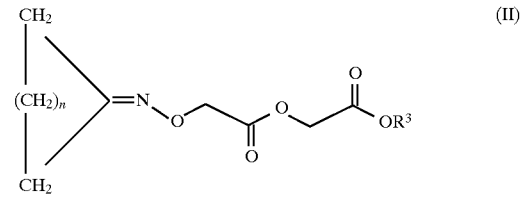

(II)

where R1 and R2 independently of one another are C1–C6-alkyl, n is 2 or 3 and R3 is hydrogen or C1–C6-alkyl. Specific inhibitors of ethylene biosynthesis or action include: {[(isopropylidene)-amino]oxy}-acetic acid-2-(methoxy)-2-oxoethyl ester, {[(isopropylidene)-amino]oxy}-acetic acid-2-(hexyloxy)-2-oxoethyl ester, {{cyclohexylidene)-amino]oxy}-acetic acid-2-(isopropyloxy)-2-oxyethyl ester (methoxy)-2-oxoethyl ester, [((isopropylidene)-amino]oxy acetic acid, aminooxy-acetic acid, aminoethoxyvinylglycine, rhizobitoxine, silver ions (e.g. silver thiosulfate), and 2,5-norbornadiene. The plant growth retardants include: compounds with quaternary ammonium, phosphonium or sulphonium moieties such as mepiquat chloride and chloromequat chloride; compounds that contain a nitrogen containing heterocycle such as paclobutrazol, uniconazole and ancymidol; compounds such as acylcylohexanediones (e.g., trinexapac-ethyl and prohexadione-Ca) and daminozide. Low rate application of the methods and compositions are preferred.

2 Claims, No Drawings

U.S. PATENT DOCUMENTS

| | | | |
|---|---|---|---|
| 4,344,857 | 8/1982 | Shasha et al. | 504/244 |
| 4,347,372 | 8/1982 | Fory et al. | 548/217 |
| 4,382,813 | 5/1983 | Shasha | 504/220 |
| 4,388,464 | 6/1983 | Kristinsson et al. | 548/136 |
| 4,486,218 | 12/1984 | Reiser et al. | 548/262 |
| 4,531,964 | 7/1985 | Shimano et al. | 548/302 |
| 4,534,783 | 8/1985 | Beestman | 71/27 |
| 4,561,880 | 12/1985 | Shimano et al. | 548/264 |
| 4,563,212 | 1/1986 | Becher et al. | 71/DIG. 1 |
| 4,594,099 | 6/1986 | Yamada et al. | 548/513 |
| 4,608,076 | 8/1986 | Gladon et al. | 504/182 |
| 4,640,709 | 2/1987 | Beestman | 71/DIG. 1 |
| 4,647,302 | 3/1987 | Reiser et al. | 514/383 |
| 4,659,722 | 4/1987 | Nakagawa et al. | 514/332 |
| 4,690,934 | 9/1987 | Yoshida et al. | 514/354 |
| 4,715,883 | 12/1987 | Lukaszczyk et al. | 504/106 |
| 4,729,783 | 3/1988 | Regel et al. | 514/383 |
| 4,743,293 | 5/1988 | Reiser et al. | 548/262 |
| 4,744,811 | 5/1988 | Schyuz et al. | 504/319 |
| 4,749,405 | 6/1988 | Reiser et al. | 514/184 |
| 4,785,048 | 11/1988 | Chao | 427/146 |
| 4,804,762 | 2/1989 | Yoshida et al. | 514/336 |
| 4,851,035 | 7/1989 | Pirrung et al. | 504/320 |
| 4,871,766 | 10/1989 | Tsuda et al. | 514/521 |
| 4,911,952 | 3/1990 | Doane et al. | 71/DIG. 1 |
| 4,923,503 | 5/1990 | Schulz et al. | 504/274 |
| 4,936,901 | 6/1990 | Surgant et al. | 504/133 |
| 4,956,129 | 9/1990 | Scher et al. | 264/4.7 |
| 4,997,642 | 3/1991 | Curtis et al. | 424/681 |
| 5,024,937 | 6/1991 | Penticoff et al. | 435/41 |
| 5,037,716 | 8/1991 | Moffat | 430/109 |
| 5,069,711 | 12/1991 | Fischer et al. | 504/246 |
| 5,078,888 | 1/1992 | Penticoff et al. | 210/639 |
| 5,087,456 | 2/1992 | Meinard et al. | 424/501 |
| 5,089,046 | 2/1992 | Lee et al. | 504/207 |
| 5,125,959 | 6/1992 | Suyama et al. | 504/253 |
| 5,126,360 | 6/1992 | Dutzmann et al. | 514/383 |
| 5,130,131 | 7/1992 | Narayanan et al. | 424/94.65 |
| 5,135,942 | 8/1992 | Dutzmann et al. | 514/383 |
| 5,139,774 | 8/1992 | Meinard et al. | 71/DIG. 1 |
| 5,160,529 | 11/1992 | Scher et al. | 71/DIG. 1 |
| 5,221,318 | 6/1993 | Fischer et al. | 504/283 |
| 5,223,526 | 6/1993 | McLoughlin et al. | 514/406 |
| 5,228,896 | 7/1993 | Misslitz et al. | 504/288 |
| 5,250,505 | 10/1993 | Kast et al. | 504/292 |
| 5,310,721 | 5/1994 | Lo | 504/116 |
| 5,330,965 | 7/1994 | Misslitz et al. | 504/244 |
| 5,332,584 | 7/1994 | Scher et al. | 424/408 |
| 5,364,834 | 11/1994 | Kirchner et al. | 504/319 |
| 5,374,609 | 12/1994 | Kast et al. | 504/344 |
| 5,403,812 | 4/1995 | Kast et al. | 504/100 |
| 5,407,896 | 4/1995 | Kast et al. | 504/100 |
| 5,420,148 | 5/1995 | Dehne et al. | 514/395 |
| 5,433,173 | 7/1995 | Markles | 119/231 |
| 5,439,926 | 8/1995 | Dutzmann et al. | 514/383 |
| 5,446,067 | 8/1995 | Benoit et al. | 514/640 |
| 5,464,769 | 11/1995 | Attree et al. | 435/240.4 |
| 5,466,460 | 11/1995 | McMahon et al. | 424/408 |

OTHER PUBLICATIONS

Beyer, et al; "Abscission: The Role of Ethylene Modification of Auxin Transport"; (1971) 48:208–212; *Plant Physiol.*

Cockshull, et al.; "2–Chloroethylphosphonic acid and flower initiation by Chrysanthemum morifolium Ramat, in short days and in long days"; (1978) 53:85–90; *Journal of Horticultural Science.*

Gianfagna, et al; "Mode of action and use of plant growth retardants in reducing the effects of environmental stress on horticultural crops"; (1992) 778–787; *Plant Growth Regulation.*

Grossmann, et al; "inhibition of Ethylene Production in Sunflower Cell Suspensions by a Novel Oxime Ether Derivatives"; (1991) 10:163–166; *Journal of Plant Growth Regulation.*

Guinn; "Abscission of Cotton Floral Buds and Bolls as Influenced by Factors Affecting Photosynthesis and Respiration"; (1974) 14:291–293; *Crop Science.*

Guinn; "Effects of Some Organic Solvents on Ethylene Evolution From Young Cotton Bolls"; (1977) 60:446–448; *Plant Physiol.*

Guinn; "Fruit Age and Changes in Abscisic Acid Content, Etylene Production, and Abscission Rate of Cotton Fruits"; (1982) 69:349–353; *Plant Physiol.*

Guinn; "Hormonal Relations in Flowering, Fruiting, and Cutout"; 265–272; *Western Cotton Research Laboratory.*

Guinn; "Nutritional Stress and Ethylene Evolution by Young Cotton Bolls"; (1976) 16:89–91; *Crop Science.*

Hoffmann; "Use of plant growth regulators in arable crops: Survey and outlook"; (1992) 798–808; *Progress in Plant Growth Regulation.*

Kirchner, et al; "Effects of novel oxime ether derivatives of aminooxyacetic acid on ethylene formation in leaves of oilseed rape and barley and on carnation flower senescence"; (1993) 13:41–46; *Plant Growth Regulation.*

Koning; "Control of Flower Opening by Plant Hormones in Gaillardia Grandifora"; (1981) 40–67; *Dissertation, University of Michigan.*

Lay–Yee, et al.; "Changes in Cotyledon mRNA during Ethylene Inhibition of Floral Induction in Pharbitis nil Strain Violet"; (1987) 84:545–548; *Plant Physiol.*

Lipe, et al; "Ethylene, a Regulator of Young Fruit Abscission"; (1973) 51:949–953; *Plant Physiol.*

Lipe, et al; "Ethlene: Role in Fruit Abscission and Dehiscence Processes"; (1972) 50:759–764; *Plant Physiol.*

Machackova, et al; "Reversal of IAA–Induced Inhibition of Flowering by Aminoethoxyvinylglycine in Chenopodium"; (1986) 4:203–209; *Journal of Plant Growth Regulation.*

Owens, et al; "Induction of Perfect Flowers on Gynoecious Muskmelon by Silver Nitrate and Aminoethoxyvinylglycine"; (1980) 15(5):654–655; *HortScience.*

Owens, et al; "Induction of Staminate Flowers on Gynoecious Cucumber by Aminoethoxyvinylglycine"; (1980) 15(3):256–257; *HortScience.*

Stanley, et al.; "The site of ethephon application and its effect on flower initiation and growth of chrysanthemum"; (1989) 64(3)341–350; *Journal of Horticultural Science.*

Suge; "Inhibition of photoperiodic floral induction in Pharbitis nil by ethylene"; (1972) 13:1031–1038; *Plant & Cell Physiol.* van Altvorst, et al; "The role of ethylene in the senescence of carnation flowers, a review"; (1995) 16:43–53; *Plant Growth Regulation.* van Doorn, et al; "Developments in the use of growth regulators for the maintenance of post–harvest quality in cut flowers and potted plants"; (1991) 298:195–208; *Acta Horticulturae.*

Veen; "Use of Inhibitors of Ethylene Action"; (1987) 201:213–222; *Acta Horticulturae.*

White, et al; "Environmental control of ethylene biosynthesis"; (1992) 147–155; *Progress in Plant Growth Regulation.*

Woltering, et al; "Amino–oxyacetic acid: analysis and toxicology"; (1987) 216:273–280; *Acta Horticulturae.*

PLANT GROWTH RETARDANTS IN COMBINATION WITH INHIBITORS OF ETHYLENE BIOSYNTHESIS OR ACTION

This application claims the benefit of U.S. Provisional Application Number 60/009,298 filed on Dec. 21, 1995.

NOTICE OF COPENDING PATENT APPLICATIONS

The following patent applications are copending in the United States Patent and Trademark Office with this application:

1. Low Rate Application of Inhibitors of Ethylene Biosynthesis or Action, U.S. patent application Ser. No. 08/770,492, filed on even date herewith (Dec. 20, 1996), and incorporated herein by reference;

2. Encapsulated Plant Growth Regulator Formulations, U.S. patent application Ser. No. 08/771,319, filed on even date herewith (Dec. 20, 1996), and incorporated herein by reference;

3. Encapsulated Plant Growth Regulator Formulations And Applications, U.S. patent application Ser. No. 08/771,734, filed on even date herewith (Dec. 20, 1996), and incorporated herein by reference.

4. Encapsulated Plant Growth Regulator Formulations In Combination With Plant Growth Retardants, U.S. patent application Ser. No. 08/771,769, filed on even date herewith (Dec. 20, 1996), and incorporated herein by reference.

5. Plant Growth Regulators In Pyrrolidone Solvents, U.S. patent application Ser. No. 08/771,769, filed on even date herewith (Dec. 20, 1996), and incorporated herein by reference;

6. Enhancing The Rate of Seed Germination With Application of Ethylene Biosynthesis Inhibitors, U.S. patent application Ser. No. 08/770,789, filed on even date herewith (Dec. 20, 1996), and incorporated herein by reference; and 7. Aminoethoxyvinylglycine in combination with a Plant Growth Regulator, U.S. patent application Ser. No. 08/777,716, filed on even date herewith (Dec. 20, 1996), and incorporated herein by reference;

FIELD OF THE INVENTION

The present invention is related generally to the field of agriculture and specifically to compositions and use of plant growth regulators.

BACKGROUND OF THE INVENTION

Agriculture workers actively seek ways to improve the economic output of commercial crops. For example, in cotton crops, workers seek to improve such growth factors as increased boll set, increased floral initiation, decreased floral abscissionincreased germination, decreased boll abscission, and enhanced root growth. Workers also seek to increase plant tolerance to environmental stress.

Formulations containing plant growth regulators (PGRs) have been developed to improve the economic yield of agricultural plants. Plant growth retardants and inhibitors of ethylene biosynthesis or action are two types of PGRs. Some plant growth retardants have been shown to inhibit gibberellin biosynthesis resulting in the reduction of shoot height in small grains and cotton. This reduction in shoot height has a strong economic benefit since it provides for less lodging in small grains and reduction of excessive vegetative growth. It also provides more uniform ripening in cotton.

Three groups of gibberellin biosynthesis inhibitors are known. The first group encompasses compounds with quaternary ammonium, phosphonium or sulphonium moieties. One example of a compound from this group is mepiquat chloride, described in U.S. Pat. No. 3,905,798 and incorporated herein by reference. Mepiquat chloride may increase cotton yields, boll load, lint yield and seed yield. Mepiquat chloride is also known to reduce vegetative growth, plant height and boll rot. Mepiquat chloride also induces uniform ripeness if the plants are treated early during their development. Chloromequat chloride is also a representative compound of this group.

The second group of plant growth retardants encompasses compounds with a nitrogen containing heterocycle such as flurprimidol, paclobutrazol, uniconazole and ancymidol.

The third group encompasses acylcylcohexanediones (such as trinexapac-ethyl and prohexadione-Ca) and damizonide.

It is known that ethylene is involved in plant senescence and plant stress reactions. Ethylene is also involved in leaf, flower, and fruit abscission. Hence, agents that inhibit or regulate the production of ethylene in plants or control its action have been developed in an effort to improve the yield of agricultural crops. Inhibitors of ethylene biosynthesis include substituted oxime-ethers as described in U.S. Pat. No. 4,744,811, incorporated herein by reference. These compounds are also described in PCT Application WO 95-02211, incorporated herein by reference, as being soil amendment compositions that increase the assimilation of nitrogen by higher plants.

Other inhibitors of ethylene biosynthesis and action include aminoethoxyvinylglycine ("AVG"), aminooxyacetic acid ("AOA"), rhizobitoxine, and methoxyvinyl glycine ("MVG"). Silver ions (e.g. silver thiosulfate), and 2,5-norbornadiene inhibit ethylene action.

Plant growth regulators have also been used to protect crops from the effects of environmental stress. Gianfagna, T. J. et al. "Mode of Action and Use of Growth Retardants in Reducing the Effects of Environmental Stress on Horticultural Crops: Karssen, C. N. et al. (eds.) *Progress in Plant Growth Regulation,* pp. 778–87 (1992). For example, researchers found that if ethephon was applied at a low rate (0.08 mM) it significantly delayed bloom in peach and reduced side effects. Researchers also found that ethephon increased the yields and hardiness of several horticultural plants.

Although PGRs have been developed as a means to improve agricultural crop yields, certain obstacles make the actual use of the PGR prohibitive. For example, many of the compounds display phytotoxicity. Other compounds are difficult to synthesize.

Many compounds require high rate applications to be effective. For example, PCT Application WO 93/07747, incorporated herein by reference, describes an improvement in a plant growth factor by applying aminoethoxyvinylglycine ("AVG"), an inhibitor of ethylene biosynthesis, to cotton plants. As the rate of AVG treatment increased, so did the improvement. (WO 93/07747, Examples 24). Assuming that a spray volume of 500 I/ha was used, the rates of application described in WO 93107747 would be approximately 62.5 to 500 g ai/ha (ai=active ingredient). The maximum rate response occurs at the highest rates.

High rate applications may result in a significant waste of material and may result in the discharge of the PGRs into the surrounding environment. Also, although many of these compounds may induce a beneficial growth habit, they do not provide consistent improvement in plant growth factors. Other compounds may lose their effectiveness or cause a reduction in yield when applied to species which are under some form of environmental stress.

Thus, it is an object of the invention to formulate a PGR that not only improves a plant growth factor but one that also reduces toxicity. It is also an object of the present invention to provide a PGR that has lower application rates and has limited environmental impact.

SUMMARY OF THE INVENTION

Provided herein is a method for improving at least one plant growth factor in a plant comprising administering to the plant a first plant growth regulator comprising an inhibitor of ethylene biosynthesis or action and a second plant growth regulator comprising a plant growth retardant.

Also provided is a composition comprising a plant growth retardant and an inhibitor of ethylene biosynthesis or action wherein the composition provides for a consistent improvement of a plant growth factor when applied to an agricultural plant.

An improvement in a plant growth factor is defined as an agronomic improvement of plant growth such as increased floral (square) initiation, increased flower retention, increased fruit retention, increased square retention, increased boll retention, increased root growth, decreased internode length, increased stress tolerance, decreased wilting, decreased senescence, darker green pigmentation, increased germination rate, increased tolerance to low temperatures, and increased crop yield. That is, a favorable alteration of the physiology or growth of plants or an increase or decrease in plant growth which leads to an economic or agronomic benefit. Improvement in growth factors that result from the inhibition of ethylene production is preferred.

DETAILED DESCRIPTION OF THE INVENTION

Embodiments of the invention contain a first plant growth regulator which includes plant growth regulators comprising an inhibitor of ethylene biosynthesis or action. A preferred inhibitor comprises a substituted oxime-ether having the formula:

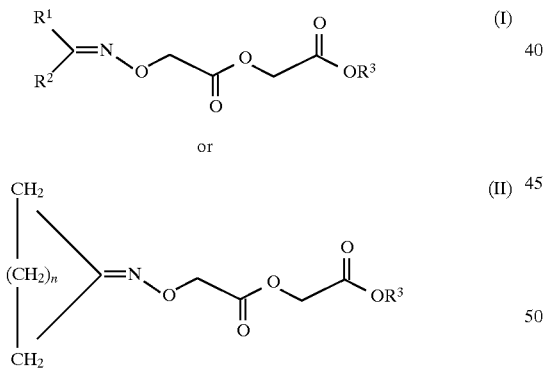

where R1 and R2 independently of one another are C1–C6-akyl, n is 2 or 3 and R3 is hydrogen or C1–C6.

Preferably, the substituted oxime-ether comprises:

1) {[(isopropylidene)-amino]oxy}-acetic acid-2-(methoxy)-2-oxoethyl ester represented by the structure:

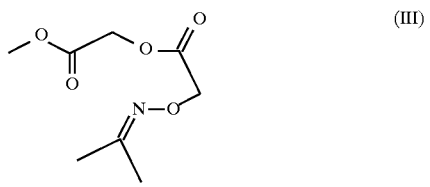

2) {[(isopropylidene)-amino]oxy}-acetic acid-2-(hexyloxy)-2-oxoethyl ester represented by the structure:

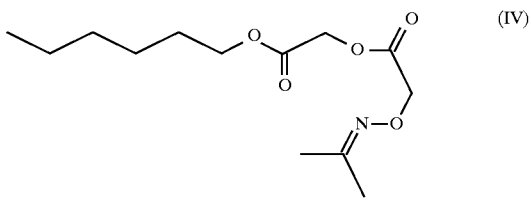

and 3) {{cyclohexylidene)-amino]oxy}-acetic acid-2-(isopropyloxy)-2-oxoethyl ester represented by the structure:

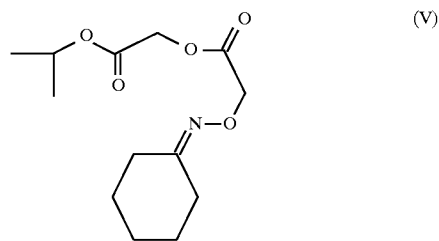

Other embodiments of the invention include, as inhibitors of ethylene biosynthesis, compounds such as [(isopropylidene)-amino]oxy acetic acid represented by the structure:

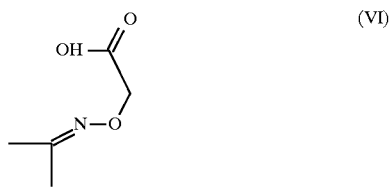

and aminooxyacetic acid represented by the structure:

Other inhibitors of ethylene biosynthesis or action that may be used to carry out the present invention include aminoethoxyvinylglycine ("AVG"), rhizobitoxine, methoxyvinyl glycine ("MVG"), silver ions (e.g. silver thiosulfate), and 2,5-norbornadiene The most preferred inhibitor of ethylene biosynthesis for use in the invention comprises {[(isopropylidene)-amino]oxy}-acetic acid-2-(methoxy)-2-oxoethyl ester.

The second growth regulator comprises growth retardants such as compounds with quaternary ammonium, phosphonium or sulphonium moieties. Examples of these compounds include mepiquat chloride and chloromequat chloride. The invention also includes other known plant growth retardants such as those compounds that contain a nitrogen containing heterocycle. Examples of these compounds include flurprimidol, paclobutrazol, uniconazole and ancymidol. The invention may also contain plant growth retardants such as acylcylohexanediones (e.g., trinexapac-ethyl and prohexadione-Ca) and daminozide. Of the compounds noted above, mepiquat chloride is the most preferred.

The method and composition of the present invention are best carried out at low rate applications. Low rate application is defined as a single application rate lower than about 50 g ai/ha. An effective number of low rate applications can be made throughout the growing season. Preferably, the low rate application is performed from one to about ten times during the growing season, most preferably from one to about four times during the growing season. Preferred embodiments of the present invention comprise single application rates ranging from about 100 mg to about 50 g ai/ha applied from one to four times during a growing season and ranging from about 500 mg ai/ha to about 10 g ai/ha applied from one to four times during a growing season. Other rates useful for carrying-out the invention include a rate of less than or equal to about 2 g ai/ha and down to about 100 mg ai/ha applied from one to four times during a growing season. The most preferred single application rate is about 500 mg/ha to about 1.5 g ai/ha applied from one to four times during a growing season.

The present invention finds its best results in horticultural and agricultural plants and crops. The invention provides consistent improvement of at least one plant growth factor in the following plants: cotton, soybean, peanut, pepper, tomato, wheat, barley, rice plant, apple, citrus, grape, corn and canola. Improvement is also found in turf.

Preferred formulations of the low rate application include those formulations that provide an ethylene inhibitor in an effective amount to obtain consistent improvement in a plant growth factor, that is, those formulations that provide statistically significant improvement (e.g., where P=0.15 or less) when compared to untreated plants wherein the improvement is obtained more than about 50% of the time, preferably more than 60% of the time, more preferably more than 75% of the time and most preferably more than 90% of the time. In a preferred embodiment of the invention, the improvement of the plant growth factor ranges ranges from about 10% to about 60% over the untreated plants or over those plants treated with mepiquat chloride.

Tests carried out at 50 g ai/ha and above provided inconsistent results.

Accordingly, the present invention provides surprising and unexpected results since it obtains superior results at low rates.

The formulations described in this invention are generally applied to the foliage prior to bud and flower development but they can also be applied to the foliage, buds, flowers, or bolls beginning at early bud development (e.g., matchhead square in cotton) in one to four sequential applications. If sequential applications are used, applications are preferably timed at approximately 10 to 14 days apart. When applied by spraying, the active ingredient is generally mixed with water as a carrier solution in a dilution sufficient to cover the area. Typically, the spray volume of the aqueous treatment solution would be about 150 to 500 I/ha for arable crops and up to about 1,500 I/ha for fruits tress. Soil drenching is another method of application that is useful when practicing the invention.

Accordingly, the present invention provides a method which improves the economic or agronomic output of agricultural crops and decreases the amount of material that needs to be used to obtain improvement in a plant growth factor.

The following examples are illustrative only and are not meant to limit the invention in any manner.

EXPERIMENTS

1. Cotton trials. Field tests with Cotton plants were conducted as follows: Cotton plots were laid out about four rows wide and 30 to 40 feet long. The center two rows of each four row plot were sprayed over the foliage, buds, blooms, and bolls with the respective applications and the outer two rows were not treated in order to provide a buffer row between plots. In most experiments each treatment was replicated four times and organized in randomized complete block design.

The first treatments were applied when the flower buds (i.e., "squares") reached the size of a "match-head", i.e. when the first square of a typical cotton plant was about the size of a matchhead and when 50% of the plants had one or more matchhead squares. Generally, the formulations, except for the mepiquat chloride, were applied at 1, 10, 20, 50 and 100 g ai/ha. The amount of formulated material to be applied to each treatment was calculated on the basis of the amount of the area to be treated with each rate. For example, a treatment applied at a rate of 1 g of the active ingredient required four applications of 0.022 g ai/ha when four plots (2133 square feet) were treated. Thus, 0.022 g of active material was mixed with one liter of water or the amount of water necessary for the treated area for the spray volume to be equivalent to about 150 to 250 I/ha.

Subsequent to the second and/or final applications the numbers and locations on the plant of the squares, flowers, and bolls were recorded, and when possible, either boll weights or seed cotton yields were obtained.

Greenhouse tests were conducted as follows: Cotton was sown in 2 to 5 liter pots in the greenhouse, approximately one plant per pot, either in field soil or soilless planting mix. Plants remained in the greenhouse, and at the matchhead square stage described in the field methods previously, treatments were applied to the foliage, squares, flowers, and/or bolls either by spraying in a laboratory chamber sprayer (e.g. Allen Machine Works, Midland, Mich.), or by placing the pots on the ground outside the greenhouse and spraying with a hand-held spray boom. Spray volumes were approximately equivalent to that described in the field methods. Plants were then returned to the greenhouse and boll counts, boll weights, or seed cotton yields were obtained from the plants.

2. Soybean trials. Soybean trials were conducted in a greenhouse. Soybean seeds were planted in 1000 ml pots in loamy sand soil, fertilized with a slow release fertilizer and allowed to germinate. Plants were thinned to two per pot. When the plants reached the third trifoliate stage, equivalent to 11 true leaves, the plants were treated with the appropriate spray solutions applied over the top of the plants to the foliage.

The plants were placed inside a laboratory spray chamber (Allen Machine Works, Midland Mich.). As noted above, the foliage was sprayed over the top in order to mimic a typical field application. The plants were returned to the greenhouse. Periodic height measurements, pod numbers, and general plant vigor assessments were conducted. At maturity (approximately six to eight weeks after spraying) the pods were harvested, counted, and the dry-weights recorded.

Control plants were either those completely untreated or those treated with mepiquat chloride (Pix® plant growth regulator) alone. Mepiquat chloride was applied either alone or in combination with the ethylene biosynthesis inhibitors at a rate of 12 to 200 g ai/ha. When applied in combination, the two compounds were applied using the same "tank-mix" spray solution. However, combinations of mepiquat chloride and ethylene biosynthesis inhibitors may also include separate applications made within 72 hours of each other on the same plants.

Other methods of applications for cotton, soybean and other crops are described below.

EXAMPLE 1

Formulations containing a mixture of {[(isopropylidene)-amino]oxy}-acetic acid-2-(methoxy)-2-oxoethyl ester (99% Technical Grade, BASF Corporation) and mepiquat chloride (PIX® plant growth regulator) were prepared by adding both active ingredients to an aqueous spray solution. Cotton plants were treated with 1 to 100 g ai/ha of the substituted oxime ether and 12, 100, or 200 g ai/ha mepiquat chloride (when used alone or in combination with the oxime ether. The formulations were applied with either two, three, or four applications during the course of the experiment at field test sites and in a greenhouse. Mepiquat chloride was used as a control. The number of squares, number of bolls, yield, plant height, and boll weight were calculated. Yield data was measured as either kg/plot or lb/a. The results are listed in Tables 1–4. The results are displayed as percent of the plants treated with mepiquat chloride ("mc") alone.

TABLE 1

Number of Squares[1]

| Rate (kg ai/ha) | 0.001 | 0.010 | 0.020 | 0.050 | 0.10 |
|---|---|---|---|---|---|
| mc | 8.3 | 8.3 | 8.3 | 8.3 | 8.3 |
| mc + tech. | 10.3 (124%) | 8.2 (99%) | 8.11 (98%) | 9.0 (108%) | 8.2 (99%) |

[1]data from mapping done after 2nd of 4 applications (Field Data)
mc = mepiquat chloride

TABLE 2

Number of Bolls

| Rate (kg ai/ha) | 0.001 | 0.010 | 0.020 | 0.050 | 0.10 |
|---|---|---|---|---|---|
| mc[1] | 7.8 | 7.8 | 7.8 | 7.8 | 7.8 |
| mc + tech[1] | 10.7 (137%) | 9.5 (122%) | 8.3 (106%) | 8.5 (109%) | 9.3 (119%) |
| mc[2] | 4.1 | 4.1 | 4.1 | 4.1 | 4.1 |
| mc + tech.[2] | 4.9 (122%) | 4.4 (107%) | 5.3 (129%) | 5.5 (134%) | 5.3 (129%) |
| mc[3] | 7.2 | 7.2 | 7.2 | 7.2 | 7.2 |
| mc + tech.[3] | 5.5 (77%) | 6.5 (90%) | 5.5(77%) | 5.8 (80%) | 5.8 (80%) |
| mc + tech.[4] |  | 86% |  |  | 82% |

[1]Four applications (field test)
[2]Three applications (field test)
[3]Four applications (greenhouse)
[4]Two applications (greenhouse)
mc = mepiquat chloride

TABLE 3

Yield

| Rate (kg ai/ha) | 0.0010 | 0.010 | 0.020 | 0.050 | 0.1 |
|---|---|---|---|---|---|
| mc[1] | 3.6 | 3.6 | 3.6 | 3.6 | 3.6 |
| mc + tech.[1] | 4.0 (111%) | 4.1(114%) | 4.3 (119%) | 3.7 (103%) | 3.4 (94%) |
| mc[2] | 2.18 | 2.18 | 2.18 | 2.18 | 2.18 |
| mc + tech.[2] | 2.66 (123%) | 2.33 (107%) | 2.67 (122%) | 2.88 (132%) | 2.39 (109%) |

[1]Four applications (field test)
[2]Three applications (field test)
mc = mepiquat chloride

TABLE 4

Weight of Bolls[1]

| rate(kg ai/ha) | 0.010 | 0.10 |
|---|---|---|
| mc (0.200 kg ai/ha) | 87% | 83% |
| mc + tech. | 116% | 97% |
| tech. | 99% | 93% |

[1]Two applications (greenhouse)
mc 32 mepiquat chloride

The data demonstrate that applications rates of less than 50 g ai/ha provided the most consistent and maximum response. Two-thirds of the cases for the number of bolls showed an improvement at application rates less than 50 g ai/ha. Similarly, two-thirds of the cases for the yield data showed a substantial improvement. An improvement was shown in over one-half of the tests for the substituted oxime ether applied at rates less than 50 g ai/ha.

Yield studies in cotton were also performed using a PVA encapsulated compositions (540S as described above). Thirty-seven trials were carried out generally as described above for cotton field studies. The mean relative yields were calculated as compared to the values obtained for the untreated plants. The results are displayed in Table 5.

TABLE 5

(Cotton) Yield

| Rate (g/ha) | 0.5 | 1 | 10 | 20 | 50 |
|---|---|---|---|---|---|
| Relative Yield | 96% | 100% | 105% | 97% | 95% |
| Frequency of Positive Yield | 18% | 43% | 59% | 18% | 25% |

The best yield results (5%) were obtained at the 10 g/ha application rates. Also, the formulation applied at 10 g/ha had the highest frequency of positive results. The yields for the formulations applied at the 0.5, 20 and 50 g/ha rates were less than the untreated plants. The results for the plants treated with 1 g/ha application rates were the same as the results obtained for the untreated plants.

The same formulations were used to treat soybean plants and compared to untreated plants, plants treated with mepiquat chloride and plants treated with {[(isopropylidene)-amino]oxy}-acetic acid-2-(methoxy)-2-oxoethyl ester. The results are listed in Table 6.

TABLE 6

(Soybeans)
Number of Pods[1]

| rate (kg ai/ha) | 0.001 | 0.010 | 0.020 |
|---|---|---|---|
| control | 18.2 | 18.2 | 18.2 |
| mc (0.012 kg ai/ha) | 19.2 (105%) | 19.2 (105%) | 19.2 (105%) |
| tech. grade | 23.2 (127%) | 18.4 (101%) | 21.6 (119%) |
| tech. + mc | 22.6 (124%) | 16.8 (92%) | 19.6 (108%) |

[1]One application (greenhouse)
mc = mepiquat chloride

In this experiment, the low rate treatment (1 g ai/ha) using the oxime-ether and mepiquat chloride combination provided a significant improvement (27%) in the number of pods when compared to the untreated control and compared to application rates higher than 1 g ai/ha.

EXAMPLE 2

Seedcotton yield studies were performed using a combination of {[(isopropylidene)-amino]oxy}-acetic acid-2-(methoxy)-2-oxoethyl ester (99% Technical Grade; BASF Corporation) and mepiquat chloride using three sequential applications. The oxime ether was applied at 50, 100, and 200 g/ha rates. Mepiquat chloride was also applied to plants alone. The mepiquat chloride was applied at 25 g/ha on all plants. The results are displayed in Table 7.

TABLE 7

Yield

| Rate (g/ha) | 50 | 100 | 200 |
|---|---|---|---|
| Tecnical grade | 103 | 103 | 97 |
| mc (25 g/ha) | 111 | 111 | 111 |
| technical grade + mc | 124 | 120 | 114 |

EXAMPLE 3

Formulations containing polyvinyl alcohol (PVA) encapsulated {[(isopropylidene)-amino]oxy}-acetic acid-2-(methoxy)-2-oxoethyl ester (99% Technical Grade; BASF Corporation) were prepared as described in U.S. patent application Ser. No. 08/771,319 entitled "Encapsulated Plant Growth Regulator Formulations" filed provisionally on even date herewith (Dec. 20, 1996). Briefly, a 10% solution of PVA in water was prepared and the pH was adjusted to about 4.1 using sodium phosphate dibasic as a buffer system. The oxime-ether was mixed into the PVA solution under high shear until a finely dispersed emulsion was obtained. A biocide (Proxel® GXI biocide) was added to the emulsion and mixed. The solution was passed once through a high shear Eiger Mini 50 (e.g., a bead mill with an 85% chamber loading of 1 mm glass beads) at 3000 RMP. A milky solution was obtained and passed through a 0.45 micron screen. A typical particle size obtained was 10 microns. The formulations prepared contained about 5% substituted oxime-ether, about 5% PVA, about 0.12% biocide, about 0.26% sodium phosphate dibasic and about 89.62% water.

The encapsulated {[(isopropylidene)-amino]oxy}-acetic acid-2-(methoxy)-2-oxoethyl ester formulations were combined with mepiquat chloride and mixed in one liter of water. Two formulations were prepared. The first formulation contained PVA with a molecular weight of 44–66K and partial degree of hydrolysis (87–89%) (AIRVOL® 523 S polyvinyl alcohol). The second formulation contained PVA with a molecular of 70–90 k and was partially hydrolyzed (87–89%). Cotton plants were treated as described above. The plants were treated and compared to plants that were treated with mepiquat chloride (application rate at about 0.012 kg ai/ha in all studies). The number of squares and bolls were measured and the results as a percent of the plants treated with mepiquat chloride alone are displayed in Tables 6–8.

TABLE 8

(Cotton)
Number of Squares[1]

| rate (kg ai/ha) | 0.001 | 0.010 | 0.020 | 0.050 | 0.10 |
|---|---|---|---|---|---|
| mc | 8.3 | 8.3 | 8.3 | 8.3 | 8.3 |
| mc + encap. w/523S | 11.3 (136%) | 10.7 (129%) | 8.7 (105%) | 9.8 (118%) | 8.9 (107%) |
| mc + encap. w/540S | 9.8 (118%) | 10.5 (126%) | 8.2 (99%) | 10.1 (122%) | 7.0 (84%) |

[1]Measured after two of four sequential applications (field test)
mc = mepiquat chloride

TABLE 9

(Cotton)
Number of Bolls

| rate (kg ai/ha) | 0.001 | 0.010 | 0.020 | 0.050 | 0.10 |
|---|---|---|---|---|---|
| mc[1] | 7.8 | 7.8 | 7.8 | 7.8 | 7.8 |
| mc + encap. w/523 S[1] | 10.0 (128%) | 8.1 (104%) | 7.3 | 7.6 | 9.2 |
| mc + encap. w/540S[1] | 9.9 (127%) | 7.6 (97%) | 9.0 (115%) | 7.3 (94%) | 6.9 (88%) |
| mc[2] | 4.1 | 4.1 | 4.1 | 4.1 | 4.1 |
| mc + encap. w/523S[2] | 5.7 (139%) | 5.3 (129%) | 5.8 (142%) | 6.2 (151%) | 6.4 (156%) |
| mc + encap. w/540S[2] | 6.2 (151%) | 8.3 (202%) | 6.1 (149%) | 6.2 (151%) | 5.9 (144%) |
| mc[3] | 7.2 | 7.2 | 7.2 | 7.2 | 7.2 |
| mc + encap. w/523S[3] | 6.2 (86%) | 7.2 (100%) | 6.5 (90%) | 6.5 (80%) | 6.2 (86%) |
| mc + encap. w/540S[3] | 9.0 (125%) | 7.0 (97%) | 7.8 (94%) | 6.8 (94%) | 7.3 (101%) |
| mc[4] | 3.35 | 3.35 |  | 3.35 |  |
| mc + encap. w/523S[4] | 3.65 (109%) | 3.90 (116%) |  | 3.95 (118%) |  |
| mc + encap. w/540S[4] | 4.22 (126%) | 3.60 (108%) |  | 3.30 (99%) |  |

[1]Four applications (field data)
[2]Three applications (field data)
[3]Four applications (field data)
[4]Collected after the second of two sequential applications
mc = mepiquat chloride

TABLE 10

| | (Cotton) Yield | | | | |
|---|---|---|---|---|---|
| rate (kg ai/ha) | 0.001 | 0.010 | 0.020 | 0.050 | 0.10 |
| mc[1] | 1365 | 1365 | 1365 | 1365 | 1365 |
| mc + 523S[1] | 1669 (122%) | 1252 (92%) | 1290 (94%) | 1138 (83%) | 1252 (92%) |
| mc + 540S[1] | 1024 (75%) | 1290 (94%) | 1328 (97%) | 1138 (83%) | 1100 (81%) |
| mc[2] | 2.18 | 2.18 | 2.18 | 2.18 | 2.18 |
| mc + 523S[2] | 2.87 (131%) | 3.25 (149%) | 2.8 (128%) | 2.76 (127%) | 2.82 (129%) |
| mc + 540S[2] | 3.43 (157%) | 3.44 (158%) | 3.57 (164%) | 3.4 (156%) | 3.27 (150%) |

[1]Four applications (field test)
[2]Three applications (field test)
mc = mepiquat chloride Examination of the data in Tables 6–8 confirms that the present invention provides consistent improvement in a plant growth factor at low rates. At the low rate application of 1 g ai/ha, the formulation provides significant improvement (about 10% to about 60%) over the mepiquat chloride treated plants.

Thirty-four additional field trials were conducted using the PVA encapsulated formulations (540S) in combination with mepiquat chloride. The mepiquat chloride was applied, for all trials, at a rate of 12 g/ha. The {[(isopropylidene)-amino]oxy}-acetic acid-2-(methoxy)-2-oxoethyl ester was applied at 0.5 g/ha, 1 g/ha, 10 g/ha, 20 g/ha and 50 g/ha. The results are displayed as a percent in Table 11.

TABLE 11

| | Relative % Yield | | | | |
|---|---|---|---|---|---|
| rate (g/ha) | 0.5 g | 1 g | 10 g | 20 g | 50 g |
| mc (12 g/ha) | 103% | 103% | 103% | 104% | 103% |
| mc + PVA Encap. Forms. | 110% | 105% | 106% | 99% | 90% |
| Frequency of Positive Yields | 64% | 72% | 77% | 56% | 25% | mc = mepiquat chloride

The results for the plants treated with mepiquat chloride alone had a mean value of 103% when compared to the untreated plants with a frequency of positives of 60% of the untreated. Maximum yield for the combination was at 0.5 g/ha rate. Significant increase was seen with the combination below 20 g/ha.

The formulations were also tested in soybeans at rates of 1, 10 and 20 g ai/ha (greenhouse) and compared to an untreated control. The formulations showed an improvement over the untreated control and were comparable to the plants treated with mepiquat chloride.

Another soybean greenhouse study was repeated with the 540s formulations. Mean yield data was obtained (seed weight) at 1, 10 and 50 g/ha. The data obtained showed a decrease in yield when measured as percent of the untreated plants (26% m 30% abd 24% at tge 1 m 10 and 50 g/ha rates respectively).

The invention has been described with reference to various specific embodiments. However, many variations and modifications may be made while remaining within the scope and spirit of the invention.

EXAMPLE 4

A greenhouse trial was conducted in cotton plants (cv. Delta Pine 50). Single plants were raised on a peat-based substrate in 5 liter containers. Water and nutrients were applied uniformly as needed. The plants were leaf-treated with aqueous sprays of PVA encapsulated {[(isopropylidene)-amino]oxy}-acetic acid-2-(methoxy)-2-oxoethyl ester (540S) in combination with mepiquat chloride the plants were treated at growth stage 61 (beginning of flowering) using approximately 500 l/ha of liquid. The plants were also treated with mepiquat chloride alone. For all studies, mepiquat chloride was applied at rates of 10 and 100 g/ha. The {[(isopropylidene)-amino]oxy}-acetic acid-2-(methoxy)-2-oxoethyl ester was applied at rates of 10 and 100 g/ha. Two days after treatment a one week drought stress was imposed onto part of the plants by reducing water supply to approximately 30% of the regular dosage. The leaves of the plants were thus permanently wilted but not killed. Bolls were harvested fresh when the old ones of the control plants had reached their final size. The shoot length, the number of bolls per plant and the fresh weight of bolls per plant were assessed and calculated. The results did not show consistent improvement over the untreated. Although some improvement was observed over untreated and mepiquat treated plants, there was also observed decreases in the shoot length and the number of bolls at both rates.

For the shoot length measurements, the results of the combination were from 84% to 93% (measured as a % of the untreated). In the drought stressed treated plants the results for the combination ranged from 93% to 99% of the untreated. The results for the 540S formulations was 100% of the untreated at 10 g/ha and 103% of the untreated at 100 g/ha (108% and 97% at the 10 g/ha and 100 g/ha, respectively, for the drought stressed plants). The plants treated with mepiquat chloride alone showed a decrease in shoot length, 95% of the untreated at 10 g/ha and 85% of the untreated at 100 g/ha (97% and 96% for the water stressed plants.

The number of bolls ranged from 84% to 102% of the untreated, for the plants treated with the combination (94% to 100% for the drought stressed plants, respectively). The number of bolls for the 540S treated plants was 100% of the untreated at the 10 g/ha and 97% of the untreated at 100 g/ha (106% and 103% for the drought stressed plants). The results for the plants treated with mepiquat chloride alone was 92% of the untreated for the plants treated at 10 g/ha and 87% of the untreated at 100 g/ha (102% and 95% for the drought stressed plants respectively).

The fresh weight bolls per plant was measured and ranged from 89% to 95% of the untreated for the plants treated with the combination (87% to 101% for the drought stressed plants respectively). The results for the 540S treated plants were 97% of the untreated at the 10 g/ha rate and 91% of the untreated at the 100 g/ha (96% and 103% for the drought stressed plants). The results for the plants treated with mepiquat chloride alone were 95% for the untreated at 10 g/ha and 87% of the untreated at 100 g/ha (96% and 113% for the drought stressed plants respectively).

EXAMPLE 5

Dryland (non-irrigated) winter wheat was grown in the field. PVA encapsulated {[(isopropylidene)-amino]oxy}-acetic acid-2-(methoxy)-2-oxoethyl ester, prepared as described in Example 2 (540S), was applied as a foliar treatments in wheat at 1, 10, 20, and 50 g ai/ha rates, beginning at elongation and continuing every 14 days thereafter for four sequential applications. The trials were conducted in a randomized complete block design, plots 10'× 40', replicated 4 times. The compositions were applied with a flat boom backpack $CO_2$ sprayer, 20 GPA, in an aqueous carrier. Upon maturity, the wheat grain was harvested with a plot combine and the grain yield was recorded. The mean values of yield of the treated plants as compared to the values obtained for the untreated plants was recorded and the data is displayed in Table 12.

TABLE 12

| | (Wheat) | | | |
|---|---|---|---|---|
| Rate | 1 g ai/ha | 10 g ai/ha | 20 g ai/ha | 50 g ai/ha |
| Yield | 110% | 107% | 113% | 111% |

(Rates expressed as per application, each application a total of 4 times)

The results show an improvements in yield up to 13% of the untreated control. However, the results were non-significant at p=0.05.

EXAMPLE 6

Cherry tomatoes were grown in a greenhouse in large pots and treated with foliar spray applications (20 GPA) of PVA encapsulated [(isopropylidene)-amino]oxy}-acetic acid-2-(methoxy)-2-oxoethyl ester, prepared as described in Example 2 (540S). The plants were treated when the 3rd cluster of fruit (youngest at the time of application) was in the small bud stage. First and second clusters were blooming. Foliar applications were of 1, 3, 10, 30, and 100 g/ha rates in aqueous solutions. The fruits were harvested at maturity, counted, and the fresh weights were recorded and compared to the untreated plants. The results, relative to the untreated plants, are displayed in Table 13.

TABLE 13

| | (Tomatoes) | | | | |
|---|---|---|---|---|---|
| Rate | 1 g | 3 g | 10 g | 30 g | 100 g |
| 3rd Cluster Yield | 97% | 121% | 105% | 85% | 85% |
| # of Fruit | 127% | 110% | 103% | 111% | 79% |
| 2nd Cluster Yield | 89% | 109% | 109% | 93% | 90% |
| # of Fruit | 92% | 96% | 98% | 91% | 95% |
| 1st Cluster Yield | 101% | 86% | 90% | 94% | 98% |
| # of Fruit | 97% | 82% | 100% | 100% | 105% |

Improvement of fresh weight was obtained at 3 and 10 g ai/ha in the 2nd and 3rd clusters, and the number of fruits improved in the 1 st cluster (30–100 g/ha) and the 3rd cluster (1 g/ha). Best results were achieved with foliar application to the young bud stage at rates of equal to or less than 10 g ai/ha. A similar trial conducted in the greenhouse on beefsteak tomatoes resulted in no improvement in fruit yields or fruit numbers.

EXAMPLE 7

[(isopropylidene)-amino]oxy}-acetic acid-2-(methoxy)-2-oxoethyl ester (Technical grade BASF Corporation) was applied as a foliar spray application to pepper plants (bud stage) grown in the greenhouse. Aqueous solutions of {[(isopropylidene)-amino]oxy}-acetic acid-2-(methoxy)-2-oxoethyl ester was applied at rates of 1, 3, 10, 30 and 100 g ai/ha rates. The fruit was harvested upon maturity, counted, and fresh weights recorded. The results were calculated as percent of the untreated plants and they are displayed in Table 14.

TABLE 14

| Rate (g/ha) | 1 | 3 | 10 | 30 | 100 |
|---|---|---|---|---|---|
| # Fruit | 121% | 115% | 124% | 112% | 117% |
| Yield | 118% | 110% | 123% | 107% | 95% |

Improvements of both fruit numbers and fresh weight yields were obtained, particularly at rates of 10 g ai/ha and below (not significant at p=0.05).

EXAMPLE 8

[(isopropylidene)-amino]oxy}-acetic acid-2-(methoxy)-2-oxoethyl ester (99% Technical Grade, BASF) and encapsulated formulations (205S, 523S, and 540S formulations), prepared as described under Example 2, were applied in 4–6 sequential foliar applications in three small-plot field trials on established turf grass (fescue, bluegrass, and zoysia turfs). Experiments were conducted in a randomized complete block with 4 replications. The treatments were applied as a foliar spray application with a spray volume of approximately 40 gallons per acre in an aqueous dilution at rates of 1, 5, 10, and 20 g ai/ha per application. After the final application, two 2-inch soil cores were taken from the first replication of each trial. The cores were washed and visually evaluated for increases in root mass. Visually obvious increases in root mass were noted in fescue in the 523S and 540S formulation treatments, in bluegrass with the technical grade (10 g and lower), and in zoysia (technical grade below 10 g/ha and the 523S formulations at all rates).

Further controlled studies were conducted in greenhouse on bentgrass and bermudagrass that had been established and mowed several times in 4 inch pots. The study was replicated 7 times. The 523S PVA formulation was applied at 1, 5, 10 and 20 g ai/ha. In one treatment method, the compound was applied in an aqueous foliar spray 24 hours prior to cutting and transplanting from the original container. In the second treatment method, the turf was cut and transplanted and then sprayed with an aqueous foliar application. In a third treatment method, the turf was cut and transplanted and treated with a 50 ml volume of aqueous solution with equivalent active ingredient as that applied in the spray applications. The transplanted turf was removed from the pots, washed, and visual observations were made. Root and shoot dry weights and root lengths measured were measured. The results for bentgrass are displayed in Table 15.

TABLE 15

| Rate (g/ha) | 1 g | 5 | 10 | 20 |
|---|---|---|---|---|
| Root Dry Wt. | 205% | 331%* | 131% | 280%* |
| Root Length | 134% | 153%* | 144%* | 123% |
| Shoot Dry Wt. | 149%* | 129%* | 115% | 145%* |

All values relative to control treated with equivalent amount of water.
*denotes significance at p = 0.05.

The data show a significant increase (p=0.05) in root dry weight and length and shoot dry weight in bentgrass when the drench method is used. The data also show a significant increase in root dry weight and length in bermudagrass with the drench application (20 g ai/ha), and increase in root dry weight with application prior to cutting (1 g ai/ha). For example, the shoot dry weight of the treated turf showed an increase over the untreated of 49%, 29%, 15% and 45% at the 1, 5, 10 and 20 g/ha rates of applications.

EXAMPLE 9

A composition containing {[(isopropylidene)-amino]oxy}-acetic acid-2-(methoxy)-2-oxoethyl ester (99% Technical Grade, BASF) in a solvent having an emulsifier system was prepared. A C8 pyrrolidone solvent (AGSOLEX® 8, 1-Octylpyrrolidone, ISP) was mixed with an emulsifier System containing a block copolymer (PLURAFAC® LF-700, BASF) and an emulsifier comprising a blend of 80% nonyl phenol ethoxylate (MAKON®, Stepan Chemical) and 20% dioctyl sulfosuccinate (AERSOL® OT 100). The resulting solution was mixed until a clear homogenous solution was formed. {[(isopropylidene)-amino]oxy}-acetic acid-2-(methoxy)-2-oxoethyl ester (99% Technical Grade, BASF) was added to the clear solution and mixed until a clear homogenous solution was formed. The resulting composition contained about 82.6% C8 pyrrolidone, about 8.3% block copolymer emulsifier, about 4.1% of the emulsifier and about 5.0% of the {[(isopropylidene)-amino]oxy}-acetic acid-2-(methoxy)-2-oxoethyl ester. This resulting composition was mixed with PIX® mepiquat chloride plant growth regulator (BASF Corporation) such that the mepiquat chloride was applied to cotton in field studies at a rate of 12 g/ha and the {[(isopropylidene)-amino]oxy}-acetic acid-2-(methoxy)-2-oxoethyl ester contained in the solvent with an emulsifier system was applied at 1 and 10 g/ha. The results are displayed in Table 16.

TABLE 16

| | (Cotton) Yield | | |
|---|---|---|---|
| Rate (g/ha) | 1 | 10 | mc |
| Relative Yield (% compared to untreated)) | 103% | 106% | 102% |
| Frequency of Positive Yield | 62% | 62% | 38% | mc = mepiquat chloride

The results show that the treated plants had a 3% and 6% increase over the untreated plants at 1 and 10 g/h rates respectively—with a frequency of positive yield of 62%.

EXAMPLE 10

Field studies were performed with mepiquat chloride (PIX® plant growth regulator) in combination with {[(isopropylidene)-amino]oxy}-acetic acid-2-(methoxy)-2-oxoethyl ester—in three formulations: 1) 99% Technical Grade, BASF Corporation; 2) PVA encapsulated (540S); and 3) solvent containing an emulsifier system (as described in Example 10). The mepiquat chloride was applied at 12 g/ha for all applications. Plants treated with mepiquat chloride alone were also evaluated for yield. The mean value for the mepiquat chloride samples was 103% over the untreated. The mean values for all combinations (as percent of yield for the mepiquat chloride treated plants) was obtained for all trials and are summarized below in Table 17.

TABLE 17

| Rate (g/ha) | Yield (%) | Number of comparisons | Frequency of positives |
|---|---|---|---|
| 0.5 | 108 | 11 | 64% |
| 1.0 | 104 | 75 | 63% |
| 10 | 104 | 83 | 55% |

The results show that the mean value of the plants treated with the combination had improvements of 8%, 4% and 4% at the 0.5, 1, and 10 g/ha rates, respectively, when compared to the mepiquat chloride treated plants. Where trials included an untreated control, combinations had improvements of 10%, 5%, and 6% when compared to the untreated controls. Mepiquat chloride applied alone resulted in an mean yield increase of 3% over the untreated control when all field trials conducted are summarized.

Experiments were also performed in drought stressed cotton. The mean values for all combinations (as percent of the plants treated with mepiquat chloride) was obtained for all trials and are summarized below in Table 18.

TABLE 18

| Rate (g/ha) | Yield (%) | Number of comparisons | Frequency of positives |
|---|---|---|---|
| 0.5 | 115 | 3 | 67% |
| 1.0 | 113 | 14 | 86% |
| 10 | 114 | 14 | 64% |

The results show that the mean value of the plants treated with the combination had improvements of 15%, 13% and 14% at the 0.5, 1, and 10 g/ha rates, respectively, when compared to the mepiquat chloride treated plants. Because the plants treated with mepiquat chloride alone showed an average (mean) increase of 9% (80% positive response; average of seven trials) over the untreated, these results indicated a 6%, 4%, and 5% improvement over the untreated plants at the 0.5, 1 and 10 g/ha rates, respectively.

The invention has been described with reference to various specific embodiments. However, many variations and modifications may be made while remaining within the scope and spirit of the invention.

We claim:

1. A method of improving yield in a cotton plant comprising administering to the foliage of the plant:
    (a) a first plant growth regulator comprising (isopropylidene)-amino]oxy}-acetic acid-2-(methoxy)-2-oxoethyl ester as an inhibitor of ethylene biosynthesis or action at a rate from about 100 mg/ha to about lower than 50 g/ha; and
    (b) a second plant growth regulator comprising mepiquat chloride.

2. The method as recited in claim 1 wherein the application rate of the first plant growth regulator is from about 500 mg/ha to about 10 g/ha.

* * * * *